United States Patent [19]

Bartish et al.

[11] 4,325,834

[45] Apr. 20, 1982

[54] HETEROGENEOUS CATALYST SUPPORTS

[75] Inventors: Charles M. Bartish, Bethlehem, Pa.; Larry J. Hayes, Roanoke, Tex.

[73] Assignee: Air Products and Chemicals, Inc., Allentown, Pa.

[21] Appl. No.: 208,902

[22] Filed: Nov. 21, 1980

[51] Int. Cl.$^3$ .......................... B01J 31/02; B01J 31/12
[52] U.S. Cl. ............................ 252/429 R; 252/431 P; 252/441; 252/447; 562/519
[58] Field of Search .................... 252/431 P, 429 R

[56] References Cited

U.S. PATENT DOCUMENTS

| | | | |
|---|---|---|---|
| 3,652,678 | 3/1972 | Allam et al. | 260/606.5 P |
| 3,832,404 | 8/1974 | Allan et al. | 260/604 HF |
| 3,907,852 | 9/1975 | Oswald et al. | 260/448.2 N |
| 3,974,227 | 8/1976 | Berthoux | 252/431 P |
| 3,987,009 | 10/1976 | Young | 260/46.5 E |
| 3,998,887 | 12/1976 | Allen | 260/606.5 P |
| 4,045,493 | 8/1977 | Trevillyan | 260/604 HF |
| 4,102,920 | 7/1978 | Bartish | 260/532 |

FOREIGN PATENT DOCUMENTS 1517552 7/1978 United Kingdom .

*Primary Examiner*—John F. Niebling
*Attorney, Agent, or Firm*—Russell L. Brewer; E. Eugene Innis; James C. Simmons

[57] ABSTRACT

Processes are taught for the substitution of at least partially amorphous carbon with mono- and bi-dentate phosphine ligands. The ligand-substituted carbon, on combination with complexed Group VI or VIII metals, such as Wilkinson's rhodium catalyst, provide stable heterogeneous catalysts useful in reactions of the Oxo type such as hydroformylation, carbonylation and in hydrogenation.

8 Claims, No Drawings

HETEROGENEOUS CATALYST SUPPORTS

TECHNICAL FIELD

This invention pertains to Group VI or VIII heterogeneous catalysts, especially those containing rhodium, useful in reactions of the Oxo type such as hydroformylation and carbonylation and in hydrogenation and to their supports.

BACKGROUND OF THE PRIOR ART

During the past decade increasing attention has been given to the improvement of complexed Group VIII metal-containing catalysts, especially those containing rhodium, for hydrogenation and the catalysis of reactions of the Oxo type such as hydroformylation and carbonylation.

Early complexed rhodium catalysts were soluble in the reaction medium. This property brought disadvantages, especially in commercial use, because the catalysts could be separated from the reaction medium only with difficulty. Some such catalysts were also volatile to a degree such that valuable metal was lost during evaporative work-up of the reaction mixture. A popular catalyst of this period was the so-called Wilkinson's catalyst, disclosed by O'Connor and Wilkinson in J. Chem. Soc. A,2065 (1968). Wilkinson's catalyst is tris(-triphenylphosphine)rhodium chloride.

Various attempts have been made to overcome the disadvantages of the soluble rhodium catalysts. For example, U.S. Pat. No. 4,102,920, commonly assigned, teaches a carbonylation process comprising the use of polydentate phosphine and arsenic complexes of rhodium. Although such catalysts are soluble, i.e., homogeneous as they are called in the art, they are possessed of lessened volatility and thus are more easily retained in the reaction mixture.

Schultz et al taught the preparation of useful insoluble, i.e., heterogenous, catalysts by impregnating active carbon with rhodium derivatives such as the nitrate and Wilkinson's catalyst, and thereafter calcining the mixture. The work was presented before the Division of Petroleum Chemistry, Inc., American Chemical Society, Boston Meeting, Apr. 9–14, 1972 (Paper p. B14).

Another approach to heterogeneous catalysts involved coordinating rhodium salts with a polymeric phosphine substrate thus conferring insolubility on the catalyst and permitting its recovery from the reaction mixture by filtration. An early contribution in this direction was made by Grubbs et al as reported in J. Amer. Chem. Soc. 93 3062 (1971). These authors chloromethylated slightly cross-linked polystyrene and reacted the resulting chlorine-containing polymer with lithium diphenyl-phosphine to produce a ligand-substituted polystyrene. Combination of the modified polymer with Wilkinson's catalyst, by coordination, produced an active, readily isolated, heterogeneous catalyst. Utility as a hydrogenation catalyst was demonstrated.

Allum et al in U.S. Pat. No. 3,652,678 and Young in U.S. Pat. No. 3,987,009 disclosed similar heterogeneous catalysts employing various insolubilizing polymers.

Allen in U.S. Pat. No. 3,998,887 disclosed catalysts of similar type which comprised a polymer derived from p-styryldiethylphosphine.

Trevillyan in U.S. Pat. No. 4.045,493 disclosed such catalysts comprising a polyphenylene polymer backbone and pendant diphenylphosphine ligand groups. Such catalysts are reported to be more thermally stable under reaction conditions than are similar catalysts derived from polyvinyl chloride and polystyrene.

British Pat. No. 1,517,552 taught a process for preparing other catalysts insolubilized by covalent attachment to various polymers. The catalysts of this patent are characterized by diphosphine bidentate ligands. Increased reaction specificity was claimed for such catalysts.

Other inventors have produced insoluble catalysts by attachment of ligand groups to inorganic solids. For example, Oswald et al in U.S. Pat. No. 3,907,852 disclosed a process for preparing heterogeneous rhodium catalysts comprising silylhydrocarbyl phosphine ligands attached to silica and metal oxides.

Allum et al in U.S. Pat. No. 3,832,404 disclosed a hydroformylation process employing various catalysts, among others a rhodium catalyst comprising a monodentate phosphine ligand attached to inorganic solids containing a hydroxyl group. Silica was a preferred solid. The catalysts were prepared by addition of diphenylphosphine to triethoxyvinyl silane to form an intermediate which was combined, for example, with cyclo-octadiene rhodium chloride to produce a rhodium complex. The complex was attached to silica by ester exchange.

SUMMARY OF THE INVENTION

It has now been found that mono- and bi-dentate ligands, i.e., $R_3P$ and $R_2$—P—R—P—$R_2$ respectively where R is an organo group and can be readily attached to carbon which is at least partially amorphous. Preferably, phosphine ligands are used. The ligand-substituted carbon is useful as a support for a chelating combination with complexed catalysts of rhodium, such as wilkinson's catalyst and other Group VI or VIII metal salts, and provides highly active heterogeneous catalysts useful in hydrogenation and in reactions of the Oxo type, including hydroformylation and carbonylation reactions. The novel catalysts are characterized by excellent stability to withstand severe reaction conditons of high acidity and temperature as is common in commercial carbonylation practice, for example, and to high pH.

DESCRIPTION OF THE PREFERRED EMBODIMENTS

It has been found that organic mono- and bi-dentate phosphine ligands are readily attached to an insolubilized, highly stable partially amorphous carbon, either directly or indirectly through a side chain group. Attachment is effected by conventionally brominating or lithiating this carbon form and then reacting the brominated or lithiated carbon with the appropriate form of phosphine ligand.

The extent of the attack on the carbon substrate by bromine or lithiating reagent, as described infra, must be sufficiently extensive to provide sufficient phosphine ligand for chelating a Group VI or VIII metal ion such as rhodium to give practical catalytic activity in the finished catalyst. For example, bromination to about 3-6 wt. % of bromine is sufficient to provide the amount of chelating ligand. Typically, this will amount to about 0.01 to 5%; phosphorus, generally 0.2-1.5%. Similarly, lithium derivatization of carbon, obtained by reaction between the carbon and an alkyl lithium should be about the same equivalent level as bromination.

The ligands employed may contain one or more phosphine groups, those containing one phosphine group being known hereinafter as monodentate ligands and those containing two such groups as bidentate ligands and those containing three are polydentate ligands. The preferred ligands are the bidentate ligands because of the greater resistance to extraction of metal from the finished catalyst. Among the bidentate ligands, those having one to three methylene groups between the phosphine groups are most preferred. These include bis(diphenylphosphino)ethane; bis(diphenylphosphino)ethylene; bis(diphenylphosphino) propane; 2-[(diphenylphosphino)methyl]-1,3 diphenyl phosphino propane and the like.

The metals suited are those Group VI and VIII metals which chelate with the ligand. Conventional metals used for the reaction suggested herein are rhodium, iridium, nickel, cobalt, platinum, palladium, and the like.

The examples following, which are not intended to be limiting, demonstrate processes for attaching mono and bi-dentate ligands to carbon and converting these intermediates to finished catalysts. The processes proceed via (a) a bromine derivative produced by direct bromination of the carbon or (b) a lithium derivative produced either by reaction between brominated carbon and alkyl lithium or by direct reaction between carbon and alkyl lithium. The lithium derivatives, unlike the bromine derivative, are not isolated but are reacted further in situ, as is usual in the art. Temperatures and pressures are those conventionally used for Friedel Crafts for alkylation reactions. Brominated carbon can be reacted with lithiated organic mono- and di-phosphines as exemplified infra. Similarly, lithiated carbon can be reacted with organic mono- and di-phosphine halides. Both reactions produce mono- and bi-dentate ligand-substituted carbon, depending on the phosphine employed. The carbon so substituted can be reacted by art known methods with Group VI or VIII metal derivatives such as Wilkinson's catalyst, optionally in the presence of carbon monoxide and/or hydrogen, to produce the finished catalyst.

The above principles are demonstrated in the examples following.

EXAMPLE 1

Bromination of Carbon

Carbon*, 12–30 mesh, (79.4 g, 6.61 moles) was suspended in carbon tetrachloride (400 ml). After addition of ferric chloride catalyst (0.8 g) and bromine (8.26 g, 0.10 moles) the mixture was stirred at room temperature for two days.

*High surface area largely amorphous carbon derived from bituminous coal and sold by Pittsburgh Carbon Company under the name of "BPL Carbon."

The carbon was filtered and washed successively with acetone, dioxane/water (1:1 vol), and with pure dioxane. Thereafter the carbon was continuously extracted with benzene/dioxane (1:1 vol) for one day. The product dried at 40° C. contained 3.59 wt. % bromine which corresponds to one bromine atom for each approximately 180 carbon atoms.

EXAMPLE 2

Preparation of a Monodentate Ligand-Substituted Carbon

The process of this example porceeds via the carbon-lithium alkylation exchange prepared by reaction between the brominated carbon of Example 1 and butyl lithium.

Brominated carbon (20 g) of example 1, which was dried at 80° C. and 0.1 mm Hg pressure, was suspended in absolute hexane (100 ml); then, tetramethylenediamine catalyst (0.76 g) and butyl lithium (6.4×10$^{-3}$ moles) in 100 ml hexane were added and the mixture was stirred at room temperature for one hour. Lithiocarbon and bromobutane were produced.

Lithiocarbon (10 g) was mixed with chlorodiphenylphosphine (1 g) in 100 ml of ether at a temperature of 35° C. for about 6 hours.

The product, believed to have the structure: Carbon—P(C$_6$H$_5$)$_2$, was filtered and continuously extracted for 15 hours with tetrahydrofuran. After drying at 80° C. and 0.1 mm Hg pressure, the product contained 0.45 wt. % phosphorus.

EXAMPLE 3

Preparation of Bidentate Ligand-Substituted Carbon via Lithiated Carbon

The process of this example, as in the preceding example, proceeds via the carbon-lithium route by exchange between the brominated carbon of Example 1 and butyl lithium. Three process steps lead from the lithium derivative, which was not isolated, to the bidentate ligand-substituted carbon, is believed to proceed as follows:

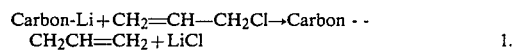     1.

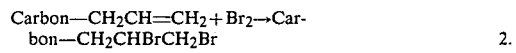     2.

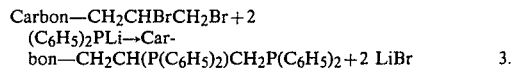     3.

The steps were carried out as follows:

1. Preparation of Carbon—CH$_2$CH=CH$_2$

Brominated carbon of Example 1 (12.5 g) was suspended in tetrahydrofuran (100 ml) containing tetramethylenediamine catalyst (0.58 g); then n-Butyl lithium (3.2 ml, 1.6 molar, 5.1×10$^{-3}$ mole) in hexane was added, and the mixture was refluxed 1.5 hours.

After cooling to room temperature, 3-chloropropene (0.38 g, 5.0×10$^{-3}$ mole) was added and the mixture was refluxed one hour. The allyl carbon product thus produced was filtered, washed with ether and acetone, and dried.

2. Preparation of Carbon—CH$_2$CHBrCH$_2$Br

The allyl carbon prepared in step 1 above was suspended in carbon tetrachloride (100 ml); then, bromine (1.65 g, 0.021 atoms) was added and the mixture stirred. The decolorized suspension was filtered, washed with ether and dried. The product contained 8.1 wt. % bromine.

3. Preparation of Carbon—CH$_2$CH(P(C$_6$H$_5$)$_2$)CH$_2$P(C$_6$H$_5$)$_2$

Diphenylphosphino lithium was prepared by adding n-butyl lithium (12.5 ml, 1.6 molar, 0.02 mole) in hexane to a solution of chlorodiphenylphosphine (3.76 g, 0.02 mole) in tetrahydrofuran. The dibromopropyl carbon of step 2 was added and the mixture was stirred for 15 hours. Water (100 ml) was added and the mixture stirred for 15 hours. Water (100 ml) was added and the product filtered. After washing with tetrahydrofuran and drying at 55° C. and 0.1 mm Hg pressure for three hours, the product contained 1.24 wt. % phosphorus.

EXAMPLE 4

Preparation of Bidentate Ligand-Substituted Carbon via Lithiated Carbon and Phosphine Halide The process of this example proceeds via lithiated carbon, prepared by exchange between butyl lithium and carbon as compared to brominated carbon in Example 3. The product has the phosphine igand bonded directly to the carbon atom. Two steps lead from the lithiated carbon to the bidentate ligand-substituted carbon, as follows:

1. Carbon—Li+Cl$_2$PCH$_2$CH$_2$PCl$_2$—Carbon—P(Cl)CH$_2$CH$_2$PCl$_2$    1.

2. Carbon—P(Cl)CH$_2$CH$_2$PCl$_2$+3 C$_6$H$_5$Li→Carbon—P(C$_6$H$_5$)CH$_2$CH$_2$P(C$_6$H$_5$)$_2$+3 LiCl    2

1. Preparation of Carbon—P(Cl)CH$_2$CH$_2$PCl$_2$

To a suspension of carbon, as described in Example 1, in tetrahydrofuran (25 g carbon in 200 ml) was added n-butyl lithium (6.8 ml, 1.6 molar, $1.1 \times 10^{-2}$ mole) and tetramethylenediamine catalyst (1.16 g) in hexane. The mixture was heated to 50° C., cooled to room temperature, and stirred for three hours.

1,2-bis(dichlorophosphino)ethane (2.3 g, $1.1 \times 10^{-2}$ mole) was added to the mixture and the mixture was stirred at room temperature for four hours.

2. Preparation of Carbon—P(C$_6$H$_5$)CH$_2$CH$_2$P(C$_6$H$_5$)$_2$

Excess phenyl lithium was added to the mixture of step 1 and stirring was continued for four hours.

The product was filtered and continuously extracted with tetrahydrofuran for 15 hours. After final washing with ether, the product was dried at 50° C. and 0.1 mm Hg pressure. It contained 1.32 wt % phosphorous.

EXAMPLE 5

Preparation of a Complexed Rhodium Catalyst Comprising a Monodentate Ligand-Substituted Carbon The above described ligand-substituted carbons can be combined with a variety of Group VI or VIII metal complexed salts by simple mixing, optionally with heating, analogous to the teachings of the above-cited art.

This example describes the preparation of a modified Wilkinson's catalyst intended particularly for hydroformylation involving the use of hydrogen and carbon monoxide.

The ligand-substituted carbon of Example 2, having the presumed structure, Carbon—P(C$_6$H$_5$)$_2$, was combined with tris(triphenylphosphine)rhodium chloride (Wilkinson's catalyst, 0.67 g, $7.24 \times 10^{-4}$ mole) in tetrahydrofuran (100 ml). The mixture was pressurized with a 1:1 (mole) mixture of hydrogen and carbon monoxide to 800 psig and held at 78° C. for 15 hours.

After filtering, washing with tetrahydrofuran, and drying at 50° C. and 0.1 mm Hg pressure, the product contained 0.54 wt. % phosphorus and 0.13 wt. % rhodium. The product was a highly active and stable hydroformylation catalyst.

EXAMPLE 6

Carbonylation of Methanol to Form Acetic Acid

This example demonstrates the use in carbonylation of a rhodium catalyst prepared from the bidentate ligand-substituted carbon of Example 4, Carbon—P(C$_6$H$_5$)CH$_2$CH$_2$P(C$_6$H$_5$)$_2$, and compares its performance to that of a corresponding catalyst prepared from diphenyl phosphine-substituted polystyrene, similar to the catalysts taught by Allen and by Grubbs supra.

The ligand-substituted supports were loaded with rhodium by heating with Wilkinson's catalyst in equivalent amount under carbon monoxide pressure in a dispersing liquid (polystyrene, toluene; carbon, acetic acid) at 80° C. and 120° C. resp. for four hours.

In comparative experiments, carbonylation of methanol was carried out in five successive charges, reusing the same catalyst in each new charge, which consisted of:

| Component | Parts by weight |
|---|---|
| Acetic acid | 16.9 |
| Methanol | 1.6 |
| HI, 50% aq. | 1.0 |

Like the charge composition, the reaction conditions were typical of commercial operation, i.e., 190° C. for four hours under 750 psig of carbon monoxide. During each run the relative rate of reaction, taken as a measure of concentration of active catalyst, was estimated by measurement of the rate of carbon monoxide consumption.

The results were the following:

| | Relative Reaction Rate | |
|---|---|---|
| Charge No. | Polystyrene Supported Catalyst | Example 4 Catalyst |
| 1 | 1 | 1 |
| 2 | 0.57 | 0.83 |
| 3 | 0.53 | 0.93 |
| 4 | 0.42 | 0.86 |
| 5 | 0.35 | 0.83 |

The results show that the carbon-comprising catalyst is substantially more stable to degradation affecting carbonylation rate than is the art-similar catalyst comprising polystyrene. The rate dropped about 20% to a value of 0.83 whereas the prior art catalyst dropped by about 60% to 0.35.

In a hydroformylation test, the invention catalyst was shown to be approximately equivalent to a bidentate ligand-substituted polystyrene suggested by British Pat. No. 1,517,552 discussed supra. However, the reaction conditions for hydroformylation are less severe than carbonylation.

We claim:

1. A heterogeneous Group VI or VIII metal salt catalyst comprising mono-or bi-dentate ligands chemically attached to at least partially amorphous carbon and an effective proportion of a Group VI or VIII metal salt.

2. A catalyst according to claim 1 wherein the metal is Group VIII.

3. A catalyst according to claim 2 wherein said mono- or bi-dentate ligands comprise phosphine groups.

4. A catalyst according to claim 3 comprising a bidentate ligand wherein said phosphine groups are separated by one or two methylene groups, and said metal is rhodium.

5. A rhodium salt catalyst according to claim 4 wherein the ligand is selected from the group consisting of:

—CH$_2$CH(P(C$_6$H$_5$)$_2$)CH$_2$P(C$_6$H$_5$)$_2$, and —P(C$_6$H$_5$)CH$_2$CH$_2$P(C$_6$H$_5$)$_2$.

6. A rhodium salt catalyst according to claim 3 wherein the ligand is —P(C$_6$H$_5$)$_2$.

7. A support for a catalytically complex composition comprising at least partially amorphous carbon and having chemically attached thereto a phosphine-containing ligand in the proportion of about 0.01 to 5% phosphorus by weight.

8. A support according to claim 7 wherein the ligand is selected from the group consisting of:

—CH$_2$CH(P(C$_6$H$_5$)$_2$CH$_2$)CH$_2$P(C$_6$H$_5$)$_2$,

—CH$_2$CH(P(C$_6$H$_5$)$_2$)CH$_2$P(C$_6$H$_5$)$_2$,

—P(C$_6$H$_5$)CH$_2$CH$_2$P(C$_6$H$_5$)$_2$, and —P(C$_6$H$_5$)$_2$.

* * * * *